United States Patent
Friedrichs (10) Patent No.: US 10,349,968 B2
(45) Date of Patent: Jul. 16, 2019

(54) DEVICES, SYSTEMS, AND METHODS FOR ESTABLISHING ELECTRICAL AND FLUID CONNECTIONS TO SURGICAL INSTRUMENTS

(71) Applicant: COVIDIEN LP, Mansfield, MA (US)

(72) Inventor: Daniel A. Friedrichs, Aurora, CO (US)

(73) Assignee: COVIDIEN LP, Mansfield, MA (US)

( * ) Notice: Subject to any disclaimer, the term of this patent is extended or adjusted under 35 U.S.C. 154(b) by 434 days.

(21) Appl. No.: 15/143,807

(22) Filed: May 2, 2016

(65) Prior Publication Data
US 2017/0311974 A1    Nov. 2, 2017

(51) Int. Cl.
A61B 17/32 (2006.01)
A61B 17/00 (2006.01)
(Continued)

(52) U.S. Cl.
CPC ........... *A61B 17/320092* (2013.01); *A61B 17/320068* (2013.01); *A61B 90/98* (2016.02); *A61B 2017/00057* (2013.01); *A61B 2017/00075* (2013.01); *A61B 2017/00115* (2013.01); *A61B 2017/00477* (2013.01); *A61B 2017/320084* (2013.01); *A61B 2018/00023* (2013.01); *A61B 2018/00172* (2013.01); *A61B 2018/00178* (2013.01); *A61B 2018/00744* (2013.01);
(Continued)

(58) Field of Classification Search
CPC ...... A61B 17/32002; A61B 17/320068; A61B 17/32006; A61B 2017/320084; A61B 2017/00075; A61F 9/00745; A61F 9/00736
See application file for complete search history.

(56) References Cited

U.S. PATENT DOCUMENTS 4,708,126 A    11/1987   Toda et al.
5,267,956 A *  12/1993   Beuchat .............. A61M 1/0058
                                                    604/153
(Continued)

FOREIGN PATENT DOCUMENTS

WO         0166026 A2    9/2001
WO      2011/031748 A1   3/2011

OTHER PUBLICATIONS

Extended European Search report issued in corresponding EP aplication No. 17168916.9 dated Sep. 28, 2017.

*Primary Examiner* — Tuan V Nguyen (57) ABSTRACT

A cartridge includes an electrical connection assembly, a first port, a second port, a pumping mechanism, a valve, and a fluid flow sensor. The electrical connection assembly is configured to electrically couple to an electrosurgical unit. The first port is configured to fluidly couple to a fluid source. The second port is configured to fluidly and electrically couple to a surgical instrument. The pumping mechanism is disposed between the first and second ports and is configured to draw fluid from the fluid source and pump the fluid to the surgical instrument. The valve is disposed between the first and second ports and is configured to selectively obstruct the flow of the fluid therethrough. The fluid flow sensor is disposed between the first and second ports and is configured to sense fluid flow therethrough. The fluid flow sensor is configured to electrically communicate with the electrosurgical unit.

10 Claims, 4 Drawing Sheets

(51) Int. Cl.
    *A61B 90/98*         (2016.01)
    *A61B 18/00*         (2006.01)
    *A61B 90/00*         (2016.01)

(52) U.S. Cl.
    CPC ............... *A61B 2018/00791* (2013.01); *A61B 2018/00863* (2013.01); *A61B 2090/0803* (2016.02); *A61B 2090/0804* (2016.02); *A61B 2090/0813* (2016.02); *A61B 2217/007* (2013.01)

(56) References Cited

U.S. PATENT DOCUMENTS

| | | | |
|---|---|---|---|
| 5,391,144 A * | 2/1995 | Sakurai | A61B 17/22012 601/3 |
| 5,637,006 A | 6/1997 | Almeras | |
| 7,238,010 B2 | 7/2007 | Hershberger et al. | |
| 7,621,766 B2 | 11/2009 | Schutz | |
| 9,050,113 B2 | 6/2015 | Bloom et al. | |
| 2002/0045851 A1 * | 4/2002 | Suzuki | A61M 1/28 604/28 |
| 2004/0147871 A1 * | 7/2004 | Burnett | A61M 5/14276 604/9 |
| 2005/0209563 A1 * | 9/2005 | Hopping | A61M 1/28 604/151 |
| 2008/0319438 A1 | 12/2008 | DeCarlo | |
| 2009/0299271 A1 * | 12/2009 | Zhang | A61M 1/28 604/29 |
| 2010/0191173 A1 * | 7/2010 | Kimura | A61B 17/320068 604/21 |
| 2011/0112472 A1 * | 5/2011 | Jacobson | A61F 9/00736 604/67 |
| 2012/0090706 A1 * | 4/2012 | Fulkerson | A61M 1/1692 137/551 |
| 2014/0276372 A1 * | 9/2014 | Eastman | A61F 9/00745 604/28 |
| 2016/0166751 A1 * | 6/2016 | Meyer | B01D 19/0068 96/157 |
| 2017/0087012 A1 * | 3/2017 | Kato | A61F 9/0017 |

* cited by examiner

DEVICES, SYSTEMS, AND METHODS FOR ESTABLISHING ELECTRICAL AND FLUID CONNECTIONS TO SURGICAL INSTRUMENTS

BACKGROUND

1. Technical Field

The present disclosure relates to devices, systems, and methods for establishing electrical and fluid connections to surgical instruments and, more particularly, to fluidly and electrically coupling a surgical instrument to a fluid source, an electrosurgical unit, and a pumping mechanism utilizing a cartridge coupled therebetween.

2. Background of the Related Art

Energy-based tissue treatment is known. Various types of energy (e.g., RF, ultrasonic, microwave, cryogenic, thermal, laser, etc.) are applied to tissue to achieve a desired result. Ultrasonic energy, for example, may be delivered to tissue to treat, e.g., coagulate and/or dissect tissue.

Ultrasonic surgical instruments, for example, typically include a waveguide having a transducer coupled thereto at a proximal end of the waveguide and an end effector disposed at a distal end of the waveguide. The waveguide transmits ultrasonic energy produced by the transducer to the end effector for treating tissue at the end effector. The end effector may include a blade, hook, ball, shears, etc., and/or other features such as one or more jaws for grasping or manipulating tissue. During use, the waveguide and/or end effector of an ultrasonic surgical instrument can reach temperatures greater than 200° C.

It is therefore be desirable to utilize a cooling fluid which circulates through the surgical instrument to avoid damage to the surgical instrument and/or the surround tissue. A typical surgical system incorporating cooling may include a surgical instrument, an electrosurgical unit having a generator, a pump, and a fluid source. During set-up, the clinician electrically couples the surgical instrument to the electrosurgical unit, fluidly couples the surgical instrument to the fluid source and the pump, primes and prepares any intermediary tubing, and ensures reliable and safe engagement of all components. Further still, disposable intermediary tubing between the various components is required to be maintained in a sterile state as any fluid pumped therethrough may inadvertently come into contact with the patient.

Thus, such surgical systems may require large amounts of time and effort for proper and safe set-up.

SUMMARY

Like reference numerals may refer to similar or identical elements. As is used in the art, the term "proximal" refers to the end of the apparatus or component thereof that is closer to the clinician and the term "distal" refers to the end of the apparatus or component thereof that is farther away from the clinician. "Clinician" refers to any medical professional (e.g., doctor, surgeon, nurse, or the like) performing or assisting with a medical procedure.

A cartridge provided in accordance with aspects of the present disclosure includes an electrical connection assembly, a first port, a second port, a pumping mechanism, a valve, and a fluid flow sensor. The electrical connection assembly is configured to electrically couple to an electrosurgical unit. The first port is configured to fluidly couple to a fluid source. The second port is configured to fluidly and electrically couple to a surgical instrument. The pumping mechanism is disposed between the first and second ports, and is configured to draw fluid from a fluid source and pump a fluid to the surgical instrument. The valve is disposed between the first and second ports, and is configured to selectively obstruct the flow of fluid therethrough. The fluid flow sensor is disposed between the first and second ports, and is configured to sense fluid flow therethrough. The fluid flow sensor is further configured to electrically communicate with the electrosurgical unit.

In an aspect, the pumping mechanism is configured to couple to the electrosurgical unit to enable the electrosurgical unit to at least one of power the pumping mechanism or control the operation thereof.

In another aspect, the pumping mechanism is one of an impeller pump, a rotary pump, or a peristaltic pump.

In yet another aspect, the valve is a pinch valve configured to couple to the electrosurgical unit to enable the electrosurgical unit to control the operation thereof.

In a further aspect, the fluid flow sensor includes an optical assembly. In yet another embodiment, the optical assembly includes a photo transmitter and a receiver configured to sense a fluid flow, and the sensed fluid flow is transmitted to the electrosurgical unit via the electrical connection assembly.

In an aspect, the fluid flow sensor is a turbine-style spinning wheel. In a further embodiment, the turbine-style spinning wheel is configured to enable determination of a fluid flow therethrough via a photo transmitter and receiver of the electrosurgical unit.

In another aspect, the cartridge comprises a device identification mechanism configured to communicate with the electrosurgical unit.

In a further aspect, the cartridge is configured to withstand sterilization.

A system provided in accordance with aspects of the present disclosure includes an ultrasonic surgical instrument, a fluid source, an electrosurgical unit, and a cartridge. The ultrasonic surgical instrument includes a removable ultrasonic transducer and an ultrasonic blade defining at least one internal lumen for circulation of fluid therethrough. The ultrasonic transducer is operably coupled to and configured to drive the ultrasonic blade. The electrosurgical unit includes a reception port having an electrical interface. The cartridge is configured to be received within the reception port, and includes an electrical connection assembly, a first port, a second port, and a pumping mechanism. The electrical connection assembly electrically is configured to engage the electrical interface of the reception port of the electrosurgical unit. The first port is configured to fluidly couple to the fluid source. The second port is configured to fluidly and electrically couple to the ultrasonic surgical instrument. The pumping mechanism is disposed between the first and second ports, and is configured to draw fluid from the fluid source and pump the fluid to the ultrasonic surgical instrument for circulation through the at least one internal lumen of the ultrasonic blade.

In an aspect, the cartridge further includes a value and a fluid flow sensor. The valve is disposed between the first and second ports, and is configured to selectively obstruct the flow of the fluid therethrough. The fluid flow sensor is disposed between the first and second ports, and is configured to sense fluid flow therethrough. The fluid flow sensor is further configured to electrically communicate with the electrosurgical unit.

In another aspect, a drive shaft of the electrosurgical unit engages the pumping mechanism.

In yet another aspect, the electrosurgical unit is configured to produce a magnetic field configured to rotate the pumping mechanism.

In a further aspect, the fluid flow sensor includes an optical assembly. In another embodiment, the optical assembly includes a photo transmitter and receiver configured to sense a fluid flow, where the sensed fluid flow is transmitted to the electrosurgical unit via the electrical connection assembly.

Further still, in an aspect the fluid flow sensor is a turbine-style spinning wheel and the electrosurgical unit includes a photo transmitter and receiver. The photo transmitter and the receiver of the electrosurgical unit are configured to determine a fluid flow though the turbine-style spinning wheel.

A kit provided in accordance with aspects of the present disclosure includes an ultrasonic transducer and a cartridge. The ultrasonic transducer is configured to couple with a surgical instrument. The cartridge includes an electrical connection assembly, a first port, a second port, a pumping mechanism, a value, and a fluid flow sensor. The electrical connection assembly is configured to electrically couple to an electrosurgical unit. The first port is configured to fluidly couple to a fluid source. The second port is configured to fluidly and electrically couple to the ultrasonic transducer. The pumping mechanism is disposed between the first and second ports, and is configured to draw fluid from a fluid source and pump a fluid to the surgical instrument via the ultrasonic transducer. The valve is disposed between the first and second ports, and is configured to selectively obstruct the flow of fluid therethrough. The fluid flow sensor is disposed between the first and second ports, and is configured to sense fluid flow therethrough. The fluid flow sensor is further configured to electrically communication with the electrosurgical unit.

In a further aspect, the kit includes a fluid source.

In another aspect, the kit includes a cable interconnecting the second port and the ultrasonic assembly.

Any of the above aspects of the present disclosure may be combined without departing from the scope of the present disclosure.

BRIEF DESCRIPTION OF THE DRAWINGS

The aspects, features, and advantages of the present disclosure will become more apparent in light of the following detailed description when taken in conjunction with the accompanying drawings in which.

DETAILED DESCRIPTION

Particular embodiments of the present disclosure are described hereinbelow with reference to the accompanying drawings. However, the disclosed embodiments are merely exemplary in nature and may be embodied in various forms. Well known functions or constructions are not described in detail to avoid obscuring the present disclosure in unnecessary detail. Therefore, specific structural and functional details disclosed herein are not to be interpreted as limiting, but merely as a basis for the claims and as an exemplification for teaching one skilled in the art to employ the present disclosure.

Figure 1:
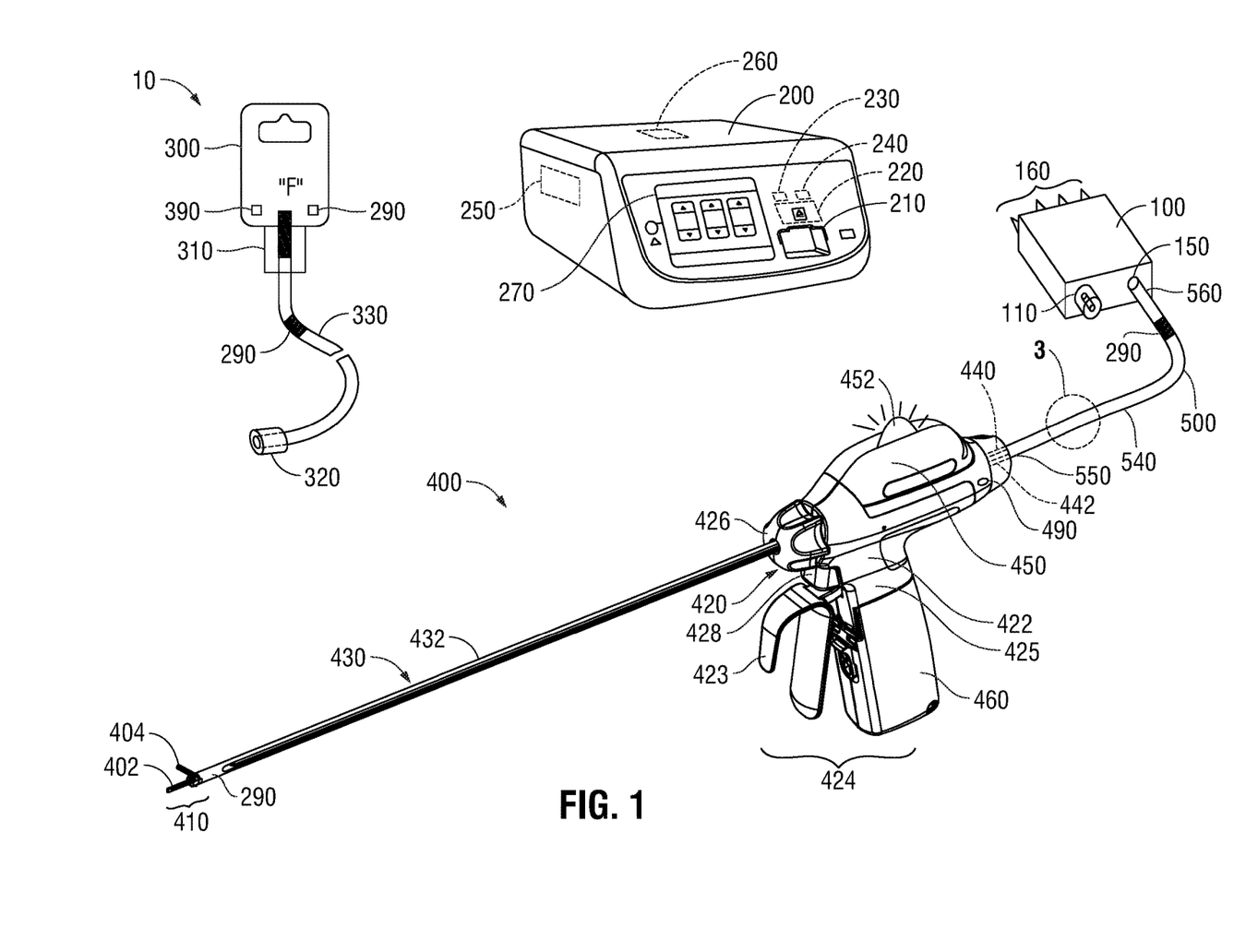
FIG. 1 is a perspective view of a surgical system provided in accordance with the present disclosure including an endoscopic ultrasonic surgical instrument, a cartridge, a fluid source, and an electrosurgical unit, wherein the system is disposed in an un-assembled state.
Figure 2:
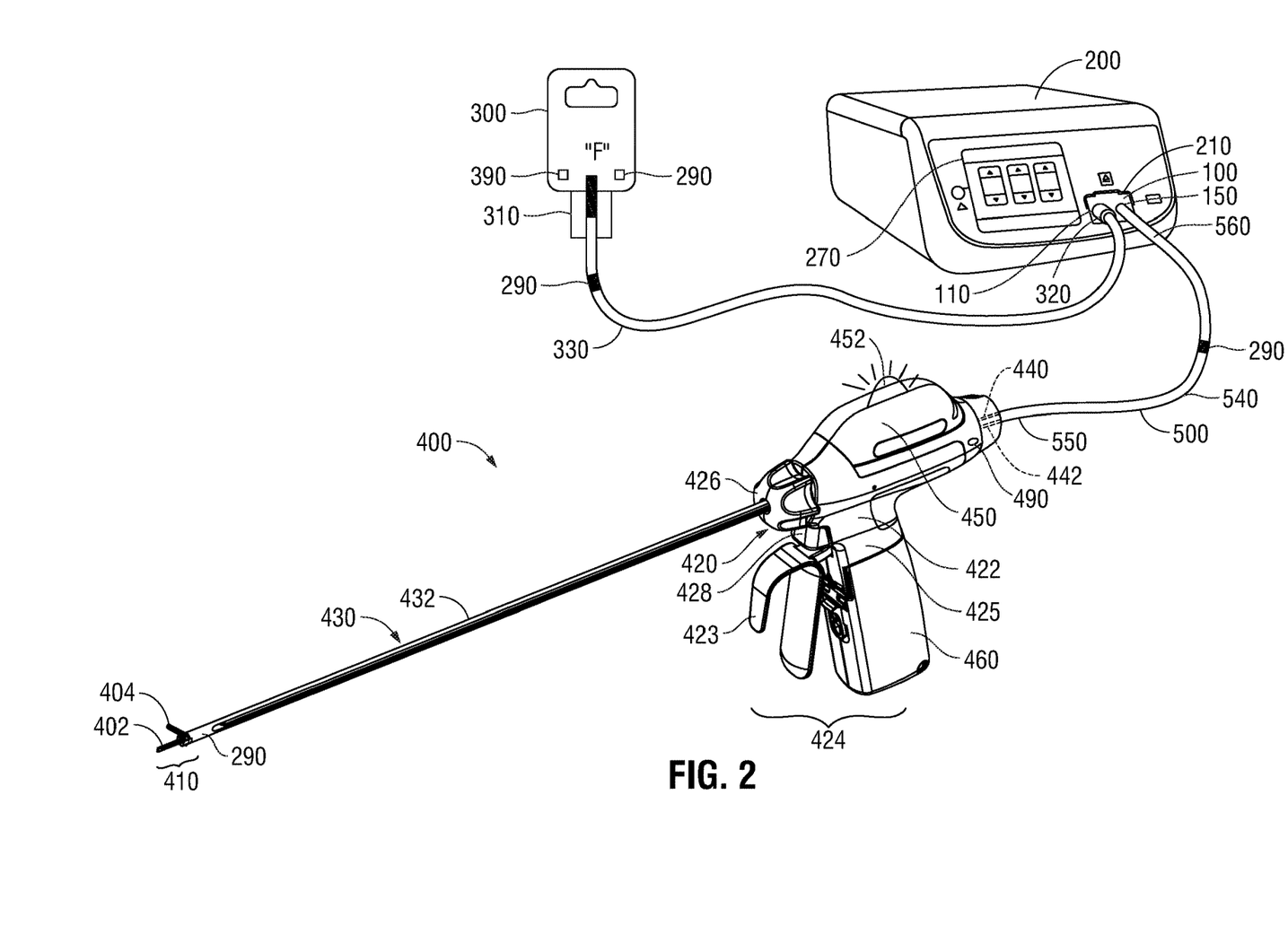
FIG. 2 is a perspective view of the surgical system of FIG. 1, with the fluid source coupled with the cartridge, and the cartridge coupled with the electrosurgical unit in an assembled state of the system.
Figure 5:
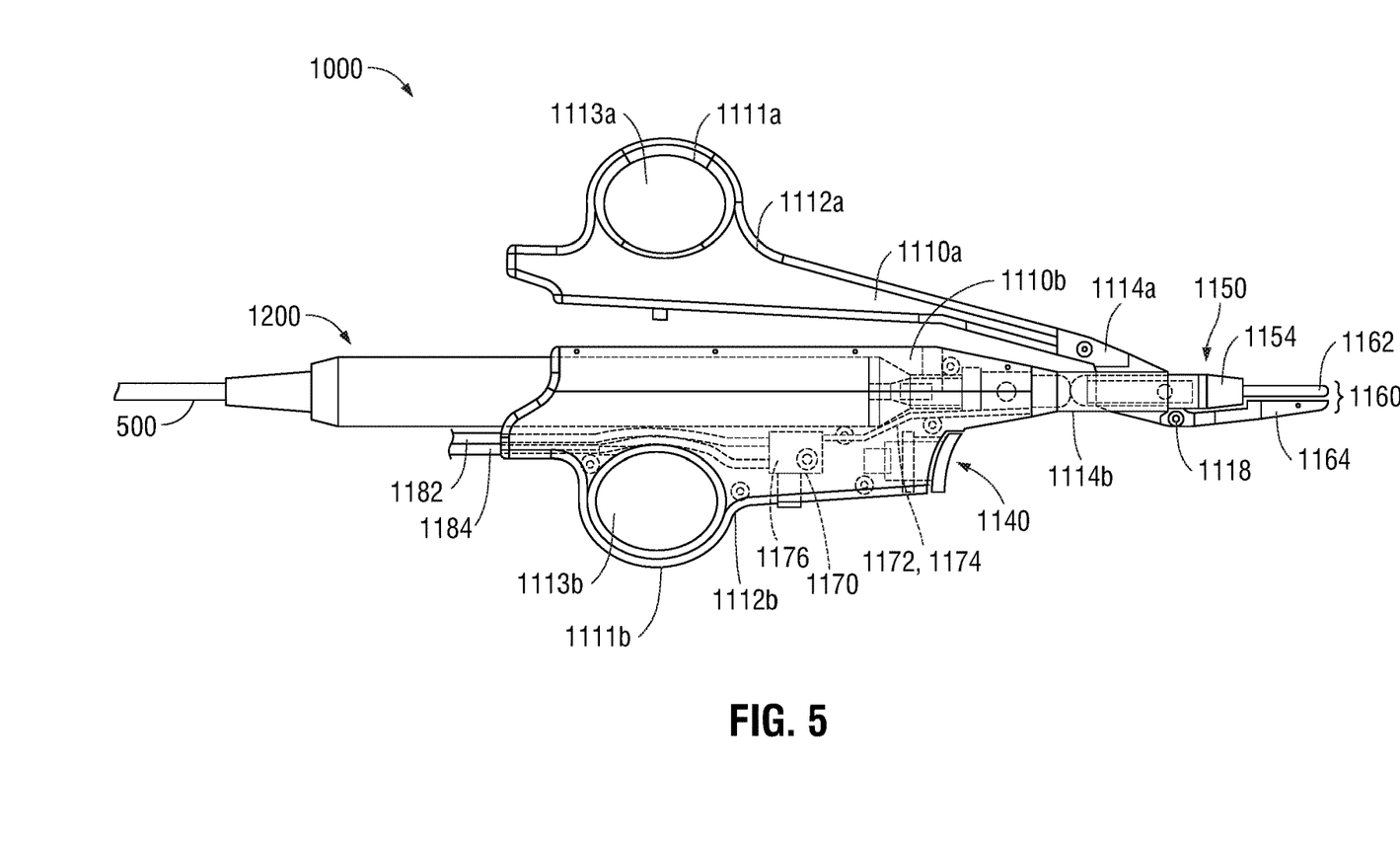
FIG. 5 is a side, cross-sectional view, of an open ultrasonic surgical instrument configured for use with the surgical system of FIG. 1.

With reference to FIGS. 1 and 2, a surgical system 10 in accordance with the aspects and features of the present disclosure generally includes a cartridge 100, an electrosurgical unit 200, a fluid source 300, and a surgical instrument, for example, an endoscopic ultrasonic surgical instrument 400. Surgical system 10 incorporates a cooling fluid "F" from fluid source 300 to cool surgical instrument 400, and more particularly, to cool a blade 402 of an end effector assembly 410 thereof. Although detailed herein below with respect to surgical instrument 400, the aspects and features of the present disclosure are equally applicable for use with any other suitable surgical system, surgical instrument, and/or cooling system. For example, the aspects and features may be provided for use with an open ultrasonic surgical instrument 1000 (FIG. 5). Obviously, different considerations apply to each particular type of system, instrument, and/or unit; however, the aspects and features of the present disclosure are equally applicable and remain generally consistent with respect to any such system, instrument, and/or unit.

Cartridge 100 is configured to fluidly couple with fluid source 300, fluidly and electrically couple with surgical instrument 400, and mate with electrosurgical unit 200. With cartridge 100 received within a reception port 210 of electrosurgical unit 200, cartridge 100 thereby interconnects surgical instrument 400 with the electrosurgical unit 200. As discussed further below, electrosurgical unit 200 is configured to provide electrical energy to surgical instrument 400, and control the flow of fluid from fluid source 300 thereto.

Figure 4:
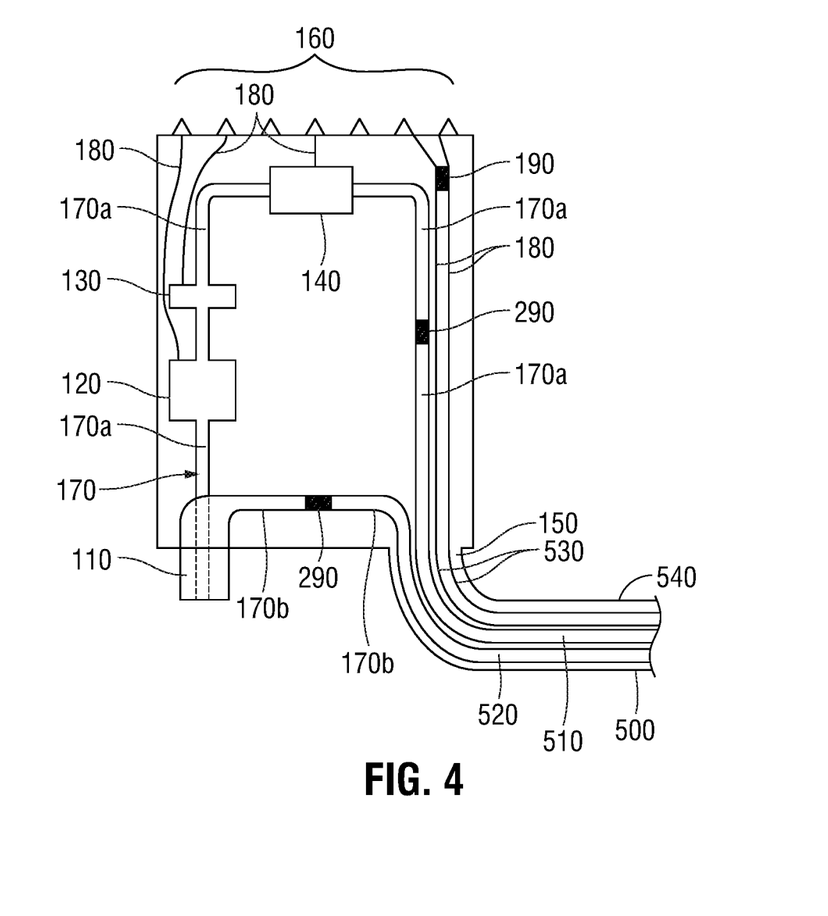
FIG. 4 is a schematic illustration of the cartridge of FIG. 1.

With reference to FIGS. 1, 2, and 4, cartridge 100 includes a first port 110, a pumping mechanism 120, a valve 130, a fluid flow sensor 140, a second port 150, and an electrical connection assembly 160. First port 110 is configured to fluidly couple with fluid source 300, and second port 150 is configured to fluidly and electrically couple with surgical instrument 400. First and second ports 110, 150 define a fluid path 170 therebetween, such that fluid "F" from fluid source 300 circulates from first port 110 to second port 150 via an output fluid path portion 170a, through surgical instrument 400, and returns back through second port 150 to first port 110 via a return fluid path portion 170b, as discussed further below. Fluid path 170 may be defined by an internal tube set, a cavity defined in cartridge 100, or combinations thereof. Pumping mechanism 120, valve 130, and fluid flow sensor 140 are disposed between first and second ports 110, 150 in fluid communication with fluid path 170 and, more specifically, along output fluid path portion 170a thereof. The electrical connection assembly 160 is configured to engage a corresponding electrical interface 220 (illustrated in phantom) disposed within reception port 210 of electrosurgical unit 200, such that cartridge 100 mates and electrically communicates with electrosurgical unit 200, as discussed below. A plurality of electrical connectors, e.g., wires 180, electrically couple electrical connection assembly 160 with pumping mechanism 120, valve 130, fluid flow sensor 140, and second port 150.

First port 110 may define a coaxial or dual lumen configuration, separate and distinct fluid port portions, or any other suitable configuration such that fluid "F" from fluid source 300 may be circulated therethrough in both directions. More particularly, first port 110 is configured to receive and return fluid "F" to and from fluid source 300, as discussed below.

Pumping mechanism 120 is configured to draw fluid "F" from fluid source 300 through first port 110 and pump fluid "F" along output fluid path portion 170a and through second port 150 for output to surgical instrument 400. Pumping mechanism 120 may define an impeller pump, a rotary pump, an electric pump, a peristaltic pump, or any other suitable pump.

Valve 130 is configured to selectively obstruct the flow of fluid "F" through output fluid path portion 170a of fluid path 170 such that a particular pressure and/or flow rate of fluid "F" circulating therethrough may be created and controlled. Valve 130 may define a solenoid, a pinch valve, or any other suitable valve which may selectively obstruct, partially or completely, the flow of fluid "F" through output fluid path portion 170a.

Fluid flow sensor 140 is configured to sense a flow rate of fluid "F" circulating through output fluid path portion 170a of fluid path 170. Fluid flow sensor 140 is configured to communicate the sensed fluid flow rate to electrosurgical unit 200, and may define an optical sensor assembly including a photo transmitter and a receiver, a turbine-style spinning wheel, and/or any other suitable flow sensor configured to sense a flow rate of fluid. More specifically, in one embodiment, the fluid flow sensor 140 includes a photo transmitter and receiver and is configured to transmit the sensed fluid flow rate to the electrosurgical unit 200 by way of wire(s) 180 and the electrical connection assembly 160. In another embodiment, wherein the fluid flow sensor 140 includes a turbine-style spinning wheel, the spinning wheel may create an optical pattern that is able to be detected by a photo transmitter 230 and receiver 240 (illustrated in phantom) of the electrosurgical unit 200 to determine the fluid flow rate.

Second port 150 is configured to electrically and fluidly couple cartridge 100 and surgical instrument 400 via a cord 500, as discussed below. Second port 150 may define a single port, as illustrated, where coupling cord 500 thereto simultaneously establishes both fluid and electrical communication between cartridge 100 and surgical instrument 400. Alternatively, second port 150 may define individual and discrete electrical and fluid connections. Further, wires 180, disposed between second port 150 and electrical connection assembly 160, electrically couple second port 150 and electrosurgical unit 200, via electrical connection assembly 160 and electrical interface 220 of electrosurgical unit 200, thereby electrically coupling surgical instrument 400 and electrosurgical unit 200.

Pumping mechanism 120, valve 130, and fluid flow sensor 140, in combination, act to pump fluid "F" to surgical instrument 400 at a desirable flow rate and/or pressure to achieve the desired cooling effects thereof. By utilizing control and monitoring features of electrosurgical unit 200, as discussed below, the desired flow rates and/or pressures may be achieved to more effectively cool surgical instrument 400. Further still, cartridge 100, and the components thereof, are configured to withstand sterilization. As cartridge 100 may be sterilized, cartridge 100 may be reused while still providing a sterile environment for fluid "F" pumped therethrough.

With reference to FIGS. 1 and 2, surgical instrument 400 generally includes a disposable handle assembly 420, a transducer and generator assembly ("TAG") 450 including a transducer and a generator, and a battery 460. Disposable handle assembly 420 includes a housing 422, a handle 424, a rotating assembly 426, an activation button 428, an elongated body portion 430, and end effector assembly 410. TAG 450 and battery 460 are releasably engagable with housing 422 of disposable handle assembly 420 and, when engaged therewith, are disposed in electrical communication with one another such that power and/or control signals can be relayed between TAG 450 and battery 460 for operating instrument 400. TAG 450 may further include an indicator 452 disposed thereon configured to notify a clinician if cooling is in effect, e.g., that pumping mechanism 120 is ON, that an error, e.g., a blockage or leakage, has occurred, and/or that at least a portion of surgical instrument 400, e.g., blade 402, has been sufficiently cooled and is ready for further use.

Elongated body portion 430 of disposable handle assembly 420 of surgical instrument 400 includes a waveguide (not shown) which extends from housing 422 to end effector assembly 410, an outer tube 432, and an inner tube (not shown). The distal end of the waveguide extends distally from outer tube 432 and defines blade 402 of end effector assembly 410, while the proximal end of the waveguide is operably coupled to TAG 450. Outer tube 432 is disposed about the waveguide and extends between housing 422 and end effector assembly 410. Rotating assembly 426 is rotatably mounted on housing 422 and operably coupled to elongated body portion 430 so as to enable rotation of elongated body portion 430 and end effector assembly 410 relative to housing 422.

End effector assembly 410 is disposed at a distal end of elongated body portion 430 and includes blade 402 and a jaw member 404. Jaw member 404 is pivotable relative to blade 402 between an open position, wherein jaw member 404 is spaced-apart from blade 402, and a closed position, wherein jaw member 404 is approximated relative to blade 402 in juxtaposed alignment therewith for clamping tissue therebetween. Jaw member 404 is operably coupled to the distal end of outer tube 432 and the proximal end of outer tube 432 is operably coupled to a movable handle 423 of handle 424, such that jaw member 404 is movable between the open position and the closed position in response to actuation of movable handle 423 relative to a fixed handle portion 425 of handle 424.

Blade 402 is configured to serve as an active or oscillating ultrasonic member that is selectively activatable to ultrasonically treat tissue grasped between blade 402 and jaw member 404. TAG 450 is configured to convert electrical energy provided by battery 460 into mechanical energy that is transmitted along the waveguide to blade 402. More specifically, TAG 450 is configured to convert the electrical energy provided by battery 460 into a high voltage alternating current (AC) waveform that drives the transducer (not shown) of TAG 450. Activation button 428 is disposed on housing 422 of disposable handle assembly 420 and is electrically coupled between TAG 450 and battery 460. Activation button 428 is selectively activatable in a first position and a second position to supply electrical energy from battery 460 to TAG 450 for operating instrument 400 in a low-power mode of operation and a high-power mode of operation, respectively. As an alternative to including the generator of TAG 450 and battery 260 on instrument 400, instrument 400 may alternatively include a transducer (removable therefrom or integral therewith) and be configured to connect to a remote generator and/or power source associated with electrosurgical unit 200. For example, a generator 250 (illustrated in phantom) of electrosurgical unit 200, powered by a wall outlet to which electrosurgical unit 200 is connected, may provide electrical energy to the transducer of instrument 400, via cartridge 100.

Figure 3:
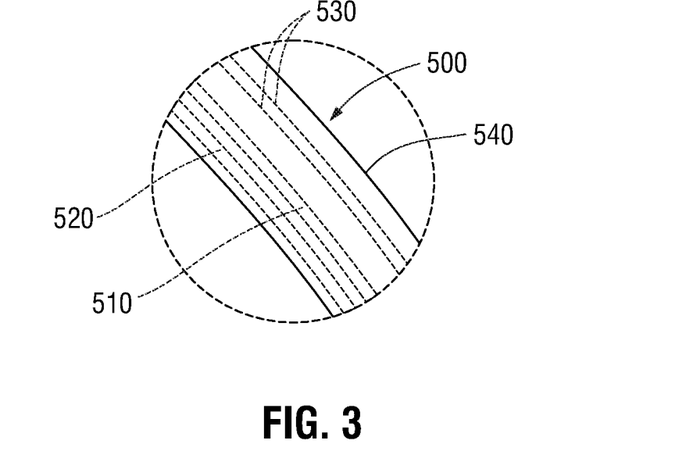
FIG. 3 is an enlarged, perspective view, of the area of detail indicated as "3" in FIG. 1.

Disposable handle assembly 420 includes at least one internal lumen, such as inflow and return conduits 440, 442, respectively, (illustrated in phantom in FIGS. 1 and 2), which extend through housing 422 and along or within at least a portion of elongated body portion 430 and into end effector assembly 410. A proximal end of inflow and return conduits 440, 442 are in fluid communication with an inflow lumen 510 and a return lumen 520 of cord 500, as illustrated in FIG. 3 and as discussed below. During cooling, fluid "F" is pumped from inflow lumen 510 through the inflow conduit 440, circulates through end effector assembly 410 (or, more specifically, blade 402 thereof), and returns through the return conduit 442 to the return lumen 520, thus facilitating cooling of end effector assembly 410.

With reference to FIGS. 1-4, cable 500 is removably coupled, or permanently secured, with either or both of surgical instrument 400 and cartridge 100, thus establishing electrical and fluid communication therebetween. A first end 550 of cable 500 may be directly or indirectly coupled with TAG 450 and/or a portion of disposable handle assembly 420, while a second end 560 of cable 500 may be coupled with second port 150 of cartridge 100. With reference to FIG. 3, cable 500 includes inflow and return lumens 510, 520 and at least one wire 530 enclosed by a common outer cover 540. Alternatively, it is envisioned that cable 500 may include separate covers for the inflow and return lumens 510, 520 and wires 530. Inflow and return lumens 510, 520 are configured to circulate fluid "F" between surgical instrument 400 and fluid source 300, via fluid path 170 of cartridge 100. Wires 530 are configured to transfer electrical energy and/or data between surgical instrument 400 and electrosurgical unit 200, via wires 180 of cartridge 100, electrical connection assembly 160 of cartridge 100, and electrical interface 220 of electrosurgical unit 200. Cable 500 may be configured to be disposable for a single use, or alternatively may be configured to withstand sterilization such that cable 500 is reusable.

Fluid source 300 is couplable with first port 110 of cartridge 100 via a transfer tube 330. Transfer tube 330 may define a coaxial tube set (FIGS. 1 and 2), may define side-by-side tube, or may define any other suitable configuration. A first end 310 of transfer tube 330 is releasably couplable with fluid source 300 and a second end 320 of transfer tube 330 is releasably couplable with first port 150 of cartridge 100, such that fluid "F" may be circulated therebetween. It is alternatively contemplated that transfer tube 330 be permanently secured to fluid source 300 and/or cartridge 100. Further, fluid source 300 and/or transfer tube 330 may be configured to withstand sterilization such that fluid source 300 and/or transfer tube 330 are reusable. Alternatively, fluid source 300 and/or transfer tube 330 may be configured to be disposable after a single use. Fluid source 300 may retain a biocompatible fluid "F" having properties to enhance thermal cooling, such as, for example, de-ionized water, sugar water, a saline solution, a dielectric solution, etc., or any combination thereof. As fluid "F" circulates through surgical system 10, thermal energy is absorbed from surgical instrument 400, thereby facilitating the cooling thereof. Fluid source 300 may define a closed-loop configuration wherein fluid "F" is continuously recirculated between fluid source 300 and surgical instrument 400, or may alternatively be configured to continuously, or selectively, dispose of spent fluid "F".

Electrosurgical unit 200 defines receiving port 210 thereon configured to receive cartridge 100 therein. It is envisioned that receiving port 210 and/or cartridge 100 may include a keying, mating, and/or locking mechanism which aligns and selectively locks cartridge 100 within receiving port 210. With electrosurgical unit 200 coupled with cartridge 100, electrical interface 220 of electrosurgical unit 200 engages electrical connection assembly 160 of cartridge 100 such that power and/or data is transferred therebetween. Electrosurgical unit 200 includes a drive mechanism 260 (illustrated in phantom) configured to engage pumping mechanism 120 of cartridge 100. Drive mechanism 260 may mechanically engage pumping mechanism 120 via a drive shaft which may articulate into and out of engagement therewith. Alternatively, drive mechanism 260 may be configured to create a magnetic field which engages pumping mechanism 120 of cartridge 100. Further, electrosurgical unit 200 may transmit electrical energy to cartridge 100, via electrical interface 220 and electrical connection assembly 160, such that pumping mechanism 120 is thereby controlled. Further still, electrosurgical unit 200 may include an internal pump (e.g., peristalsis pump) which may selectively engage transfer tube 330, and/or a portion of fluid path 170 of cartridge 100, such that the pumping of fluid "F" therethrough is thereby controlled. However, it should be appreciated that any of the fluid pumping configurations disclosed herein, and any suitable alternative fluid pumping configurations, may be utilized by cartridge 100 and system 10.

Electrosurgical unit 200 is configured to provide and control the transfer of electrical energy to the internal components of cartridge 100 and, in some embodiments, to surgical instrument 400. Further, electrosurgical unit 200 controls the flow of fluid "F" from fluid source 300 to surgical instrument 400. Electrosurgical unit 200 includes a processor and a memory to store instructions for execution by the processor for the purposes detailed herein. A user interface 270, in combination with the processor and the memory, provides a clinician the ability to control and/or monitor the flow of fluid "F" to instrument 400. In embodiments where TAG 450 and battery 460 are provided on instrument 400, electrosurgical unit 200 may provide control signals thereto for controlling the operation thereof. In embodiments where the generator is disposed within electrosurgical unit 200 and a remote power source is used, electrosurgical unit 200 may control the transfer of electrosurgical energy to the transducer of instrument 400 for controlling the output thereof. In either of these configurations, user interface 270 may facilitate the control and/or monitoring of energy delivery. User interface 270 may further provide a notification to the clinician of the operational state of electrosurgical unit 200 and/or surgical instrument 400 during operation thereof (e.g., the status of energy being transferred, the status and temperature of fluid "F" being circulated, ON/OFF indicators representative of TAG 450, fluid or electrical transfer rates, error states of electrical or fluid transfer, etc.). It is further envisioned that a wireless transmitter and receiver (not shown) of electrosurgical unit 200 may provide the clinician the ability to wirelessly control electrosurgical unit 200 at a remote location.

In embodiments, one or more temperature sensors 290 (FIGS. 1, 2, and 4) configured to sense a temperature of the fluid "F" may be disposed on or within fluid source 300, transfer tube 330, fluid path 170 of cartridge 100, inflow or return lumens 510, 520 of cord 500, and/or surgical instrument 400. In such embodiments, the electrosurgical unit 200 may be configured to determine a temperature differential between the temperature of fluid "F" pumped into surgical instrument 400 and the temperature of fluid "F" returned from surgical instrument 400. The electrosurgical unit 200 may further be configured to control the flow of fluid "F" depending on the differential, e.g., whether the differential exceeding a threshold differential, falls below a threshold differential, varies outside a particular range, etc.

In embodiments, cartridge 100 further includes a device identification mechanism 190 configured to communicate with electrosurgical unit 200 via wired communication (i.e., wires 180 and electrical connection assembly 160) and/or wireless communication (e.g., Bluetooth, Wi-Fi, ZigBee, Infrared, radio-frequency identification (RFID), etc.). Device identification mechanism 190 provides information regarding cartridge 100 and surgical instrument 400, such as, for example, an identification number of cartridge 100; the number of procedures conducted or sterilization cycles encountered by cartridge 100; the fluid flow rate and thermal temperature operating parameters of cartridge 100; the type of pumping mechanism 120 and working parameters thereof; the operating parameters, cooling requirements, and identification of TAG 450 and/or surgical instrument 400 coupled with cartridge 100, via a corresponding identification mechanism 490 disposed on surgical instrument 400 and in communication with device identification mechanism 190; the thermal properties and identification of fluid "F" of fluid source 300 coupled with cartridge 100, via a corresponding identification mechanism 390 disposed on fluid source 300 and in communication with device identification mechanism 190; etc.

Turning now to FIG. 5, another surgical instrument provided in accordance with the present disclosure, open ultrasonic surgical instrument 1000, is detailed. Open ultrasonic surgical instrument 1000 is configured to operably couple with cartridge 100 and electrosurgical unit 200 in a similar fashion as surgical instrument 100 (see FIGS. 1 and 2). Thus, for the sake of brevity, only differences will be noted hereinbelow. Open ultrasonic surgical instrument 1000 generally includes two elongated shaft members 1110a, 1110b, an activation button 1140, an elongated body portion 1150, an end effector assembly 1160, a tube assembly 1170, and a transducer assembly 1200.

Each shaft member 1110a, 1110b includes a handle 1111a, 1111b disposed at the proximal end 1112a, 1112b thereof. Each handle 1111a, 1111b defines a finger hole 1113a, 1113b therethrough for receiving a finger of the clinician. One of the shaft members, e.g., shaft member 1110a, includes a jaw member 1164 of end effector assembly 1160 extending from a distal end 1114a thereof. The other shaft member, e.g., shaft member 1110b, supports elongated body portion 1150 and transducer assembly 1200 thereon. Shaft members 1110a, 1110b are pivotably coupled to one another towards the distal ends 1114a, 1114b, respectively, thereof via a pivot pin 1118.

Elongated body portion 1150 of shaft member 1110b includes a waveguide which extends from transducer assembly 1200 to end effector assembly 1160, and an outer sleeve 1154 surrounding the waveguide. The distal end of the waveguide extends distally from outer sleeve 1154 and defines a blade 1162 of end effector assembly 1160, while the proximal end of the waveguide is operably coupled to transducer assembly 1200. Blade 1162 may define a straight or curved configuration. Blade 1162 may be curved in any direction relative to jaw member 1164, for example, such that the distal tip of blade 1162 is curved towards jaw member 1164, away from jaw member 1164, or laterally (in either direction) relative to jaw member 1164. Due to the pivotable coupling of shaft members 1110a, 1110b towards the distal ends 1114a, 1114b, respectively, thereof, handles 1111a, 1111b may be pivoted relative to one another to thereby pivot jaw member 1164 relative to blade 1162 between an open position, wherein jaw member 1164 is spaced-apart from blade 1162, and a closed position, wherein jaw member 1164 is approximated relative to blade 1162 in juxtaposed alignment therewith for clamping tissue therebetween.

Transducer assembly 1200 is configured to convert electrical energy provided by electrosurgical unit 200 (FIGS. 1 and 2), supplied via cable 500, into mechanical energy which is transmitted along the waveguide to blade 1162. Transducer assembly 1200 may be permanently affixed to elongated body portion 1150 or may be removable therefrom. Activation button 1140 is disposed on one of the shaft members, e.g., shaft member 1110b, and, similarly as detailed above with respect to instrument 400 (FIGS. 1 and 2), is selectively activatable in a first position and a second position to supply electrical energy to transducer assembly 1200 for operating surgical instrument 1000 in a low-power mode of operation and a high-power mode of operation, respectively.

Tube assembly 1170 includes at least one lumen therethrough, such as inflow and return conduits 1172, 1174, respectively, which run through surgical instrument 1000 to cool at least a portion thereof, such as, end effector assembly 1160, similar to that of surgical instrument 400. As such, during cooling, fluid "F" is pumped through inflow conduit 1172, exits a distal end of inflow conduit 1172, circulates through a portion of waveguide and blade 1162 thereof, is received by a distal end of return conduit 1174, and is pump out through return conduit 1174. A tube splitter 1176 of tube assembly 1170 is disposed within one of the shaft members, e.g., shaft member 1110b, of surgical instrument 1000. Tube splitter 1176 receives a proximal end of conduits 1172, 1174, and routes the flow of fluid "F" to/from conduits 1172, 1174 and a respective connector tube 1182, 1184. Connector tubes 1182, 1184, in turn, are coupled with inflow and return lumens 510, 520 (FIG. 3) of cord 500, to enable the inflow and outflow of fluid "F" to/from conduits 1172, 1174.

Referring generally to FIGS. 1-5, it should be appreciated that surgical instrument 400 and 1000 operate in a similar manner with respect to cartridge 100, electrosurgical unit 200, and fluid source 300 of surgical system 10. Thus, the operation of surgical system 10, and kits associated therewith, will be described herein with reference to surgical instrument 400 for the sake of brevity.

With reference to FIGS. 1-4, the operation of surgical system 10, and specifically cartridge 100, will be described. A clinician couples fluid source 300 and first port 110 of cartridge 100 via transfer tube 330, and couples cord 500 with second port 150 of cartridge 100 and surgical instrument 400. In an embodiment, cord 500 is permanently secured with second port 150 and TAG 450, such that coupling of TAG 450 to surgical instrument 400 couples cord 500 thereto. Cartridge 100 is next (or prior thereto) inserted into reception port 210 of electrosurgical unit 200, such that electrical connection assembly 160 of cartridge 100 couples with electrical interface 220 of electrosurgical unit 200. As noted above, a clinician may initiate, control, and monitor the flow of fluid "F" from fluid source 300 to surgical instrument 400 via user interface 270 of electrosurgical unit 200. The clinician may further initiate, control, and monitor the supply of energy to surgical instrument 400 (in embodiments where the generator is disposed within electrosurgical unit 200) or control and monitor TAG 450 and/or battery 460 (in embodiments where the generator and battery 460 are disposed on instrument 400).

Utilizing device identification mechanism 190, electrosurgical unit 200 may determine and implement operating parameters and control thresholds of cartridge 100, fluid source 300, and/or surgical instrument 400 as discussed above. Further, electrosurgical unit 200 may control the operation of cartridge 100, fluid source 300, and/or surgical instrument 400 via temperature sensors 290 and a preset temperature threshold for fluid "F." Alternatively or additionally, the operating parameters and control thresholds of surgical system 10 may be manually input by a clinician.

After completion of a procedure, a clinician uncouples fluid source 300 and cord 500 from cartridge 100. In an embodiment wherein cord 500 is permanently secured to second port 150 and TAG 450, TAG 450 is uncoupled from surgical instrument 400. Cartridge 100 and/or cord 500 and TAG 450 may then be sterilized, such that cartridge 100 and/or cord 500 and TAG 450, may be reused.

With reference to FIGS. 1-5, a kit for performing a surgical procedure in accordance with the present disclosure will be described, which includes at least one cartridge 100. It is envisioned that the kit may further include at least one cord 500 (separate from or formed with the at least one cartridge 100). Further still, the kit may include at least one TAG 450 (or a transducer thereof, in embodiments where the generator is not mountable on the instrument but, rather, is disposed within the electrosurgical unit 200), particularly in configurations where cord 500 is formed with TAG 450. The kit may additionally include fluid source 300 and/or transfer tube 330. It is envisioned that any of the kits disclosed herein may be configured to withstand sterilization, such that cartridge 100, and any components provided therewith, may be reused.

It should be understood that the foregoing description is only illustrative in nature. Various alternatives and modifications can be devised by those skilled in the art without departing from the disclosure. Accordingly, the present disclosure is intended to embrace all such alternatives, modifications, and variances. The embodiments described with reference to the attached drawing are presented only to demonstrate certain examples of the disclosure. Other elements, steps, methods, and techniques that are insubstantially different from those described above and/or in the appended claims are also intended to be within the scope of the disclosure.

What is claimed is:

1. A system, comprising:
    an ultrasonic surgical instrument including a removable ultrasonic transducer and an ultrasonic blade defining at least one internal lumen for circulation of fluid therethrough, the ultrasonic transducer operably coupled to and configured to drive the ultrasonic blade;
    a fluid source;
    an electrosurgical unit including a reception port having an electrical interface; and
    a cartridge configured to be received within the reception port, the cartridge including:
        an electrical connection assembly configured to engage the electrical interface of the reception port of the electrosurgical unit;
        a first port configured to fluidly couple to the fluid source;
        a second port configured to fluidly and electrically couple to the ultrasonic surgical instrument;
        an output flow path extending between the first and second ports;
        an input flow path extending between the first and second ports;
        a pump disposed along the output flow path between the first and second ports and configured to draw fluid from the fluid source and pump the fluid through the output flow path and the second port to the ultrasonic surgical instrument for circulation through the at least one internal lumen of the ultrasonic blade, wherein fluid is returned from the ultrasonic surgical instrument through the second port and into the input flow path; and
        output and input temperature sensors disposed along the output and input flow paths, respectively, the output and input temperature sensors configured to electrically communicate with the electrosurgical unit to enable determination of a temperature differential between fluid flowing through the output flow path and fluid flowing through the input flow path.

2. The cartridge of claim 1, wherein the pump is one of an impeller pump, a rotary pump, or a peristaltic pump.

3. The system of claim 1, wherein the cartridge further comprises a device identification mechanism configured to communicate with the electrosurgical unit.

4. The system of claim 1, wherein the cartridge further includes:
    a valve disposed along the output flow path between the first and second ports and configured to selectively obstruct the flow of the fluid therethrough; and
    a fluid flow sensor disposed along the output flow path between the first and second ports and configured to sense fluid flow therethrough, the fluid flow sensor configured to electrically communicate with the electrosurgical unit.

5. The system of claim 4, wherein the fluid flow sensor is a turbine-style spinning wheel.

6. The system of claim 5, wherein the turbine-style spinning wheel is configured to enable determination of a fluid flow therethrough via a photo transmitter and receiver of the electrosurgical unit.

7. The system of claim 4, wherein the fluid flow sensor includes an optical assembly.

8. The system of claim 7, wherein the optical assembly includes a photo transmitter and receiver configured to sense a fluid flow, and wherein the sensed fluid flow is transmitted to the electrosurgical unit via the electrical connection assembly.

9. The system of claim 1, wherein a drive shaft of the electrosurgical unit engages the pump.

10. The system of claim 1, wherein the electrosurgical unit is configured to produce a magnetic field to operate the pump.

* * * * *